(12) United States Patent
Hakimuddin

(10) Patent No.: US 10,884,084 B2
(45) Date of Patent: Jan. 5, 2021

(54) SYSTEMS AND METHODS FOR TRI-AXIAL NMR TESTING

(71) Applicant: Saudi Arabian Oil Company, Dhahran (SA)

(72) Inventor: Mustafa Hakimuddin, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/025,791

(22) Filed: Jul. 2, 2018

(65) Prior Publication Data

US 2018/0335494 A1      Nov. 22, 2018

Related U.S. Application Data

(63) Continuation-in-part of application No. 14/018,557, filed on Sep. 5, 2013, now Pat. No. 10,048,336.

(51) Int. Cl.
*G01R 33/46* (2006.01)
*G01R 33/30* (2006.01)
(Continued)

(52) U.S. Cl.
CPC .......... *G01R 33/46* (2013.01); *G01N 24/081* (2013.01); *G01N 33/2888* (2013.01);
(Continued)

(58) Field of Classification Search
CPC ...... G01R 33/44; G01R 33/305; G01R 33/28; G01N 33/28; G01N 24/081; G01N 3/10; G01V 3/32; G01V 3/14
See application file for complete search history.

(56) References Cited

U.S. PATENT DOCUMENTS

| | | |
|---|---|---|
| 4,671,102 A | 6/1987 | Vinegar et al. |
| 5,134,271 A | 7/1992 | Sondergeld et al. |

(Continued)

FOREIGN PATENT DOCUMENTS

| | | |
|---|---|---|
| EP | 0372636 A2 | 6/1990 |
| SU | 1508147 A1 | 9/1989 |
| WO | 2004074762 A2 | 9/2004 |

OTHER PUBLICATIONS

PCT Communication Relating to the Results of the Partial International Searching Authority; dated Nov. 18, 2014; International Application No. PCT/US2014/051418; International File Date: Aug. 18, 2014.

(Continued)

*Primary Examiner* — Walter L Lindsay, Jr.
*Assistant Examiner* — Laura Roth
(74) *Attorney, Agent, or Firm* — Bracewell LLP; Constance G. Rhebergen; Linda L. Morgan

(57) ABSTRACT

Systems and methods for testing properties of a test sample with a tri-axial nuclear magnetic resonance include a tri-axial load frame encasing a tri-axial load cell having a tri-axial sample holder and a piston assembly. A radial space surrounds the tri-axial sample holder. The tri-axial load frame further encases at least one end cap operable to contact the tri-axial load cell, and a nuclear magnetic resonance instrument. An axial pressure line is in fluid communication with the piston assembly, a confining pressure line is in fluid communication with the radial space, and a pore pressure line in fluid communication with the test sample. The axial pressure line, the confining pressure line, and the pore pressure line are independent and separate fluid flow paths.

7 Claims, 1 Drawing Sheet

(51) Int. Cl.
  *G01N 24/08* (2006.01)
  *G01V 3/14* (2006.01)
  *G01R 33/28* (2006.01)
  *G01V 3/32* (2006.01)
  *G01N 33/28* (2006.01)
  *G01N 3/12* (2006.01)

(52) U.S. Cl.
  CPC ......... *G01R 33/286* (2013.01); *G01R 33/305* (2013.01); *G01V 3/32* (2013.01); *G01N 3/12* (2013.01); *G01N 2203/0256* (2013.01); *G01V 3/14* (2013.01)

(56) References Cited

U.S. PATENT DOCUMENTS

| | | | |
|---|---|---|---|
| 5,159,828 | A | 11/1992 | Steiger et al. |
| 5,253,529 | A | 10/1993 | Lenormand et al. |
| 5,265,461 | A | 11/1993 | Steiger et al. |
| 5,275,063 | A | 1/1994 | Steiger et al. |
| 5,325,723 | A | 7/1994 | Meadows et al. |
| 5,493,226 | A | 2/1996 | Honarpour et al. |
| 5,568,262 | A | 10/1996 | Lachapelle et al. |
| 6,609,067 | B2 | 8/2003 | Tare et al. |
| 6,833,699 | B2 | 12/2004 | Galford et al. |
| 6,971,260 | B2 | 12/2005 | Potter |
| 7,042,802 | B2 | 5/2006 | Sinha |
| 7,055,374 | B2 | 6/2006 | Abdel-Hadi et al. |
| 7,274,992 | B2 | 9/2007 | Dewhurst et al. |
| 7,472,022 | B2 | 12/2008 | Birchwood |
| 7,555,414 | B2 | 6/2009 | Calhoun et al. |
| 7,793,552 | B2 | 9/2010 | Ng |
| 8,024,960 | B2 | 9/2011 | Fleury et al. |
| 8,301,383 | B2 | 10/2012 | Birchwood et al. |
| 8,443,661 | B1 | 5/2013 | Hongfeng |
| 2004/0202401 | A1 | 10/2004 | Berg |
| 2005/0103094 | A1 | 5/2005 | Knight et al. |
| 2005/0150273 | A1 | 7/2005 | Potter |
| 2005/0183859 | A1* | 8/2005 | Seams ................... E21B 43/006 166/263 |
| 2006/0070425 | A1 | 4/2006 | Lasswell et al. |
| 2010/0274367 | A1 | 10/2010 | Kaufman et al. |
| 2010/0313645 | A1 | 12/2010 | Doman et al. |
| 2011/0050223 | A1 | 3/2011 | Balcom et al. |
| 2012/0118041 | A1* | 5/2012 | He ............................ G01N 7/14 73/23.35 |
| 2012/0151998 | A1 | 6/2012 | Willberg et al. |
| 2012/0304763 | A1 | 12/2012 | Troxler |
| 2013/0228019 | A1* | 9/2013 | Meadows ................ G01N 3/08 73/821 |
| 2015/0061669 | A1 | 3/2015 | Hakimuddin |
| 2015/0061670 | A1 | 3/2015 | Fordham |

OTHER PUBLICATIONS

Han, H., et al.; High Pressure Magnetic Resonance Imaging With Metallic Vessels; Journal of Magnetic Resonance; Elsevier, Inc; Sep. 10, 2011; vol. 213; pp. 90-97.

Skagius, K., et al.; Diffusivity Measurements and Electrical Resistivity Measurements in Rock Samples Under Mechanical Stress; Water Resources Research; vol. 22, No. 4, pp. 570-580, Apr. 4, 1986.

Wang, Z., et al.; Simultaneous core sample measurements of elastic properties and resistivity at reservoir conditions employing a modified triaxial cell—a feasibility study, Geophysical Prospecting, EAGE, 57: 1009-10206.

Chryssanthakis, P, et al.; High temperature triaxial tests with ultrasonic measurements on Ekofisk chalk, Rock Mechanics for Industry, Proceedings of the 37th Rock Mechanics Symposium, pp. 373-379, 1999.

International Search Report and Written Opinion for related PCT application PCT/US2019/040100 dated Sep. 30, 2019.

International Search Report and Written Opinion for related PCT application PCT/US2014/061313 dated Feb. 25, 2015.

Josh et al., "Laboratory characterization of shale properties", Journal of Petroleum Science and Engineering, 2012, pp. 107-124, vol. 88-89, Elsevier.

Kenyon et al., "NMR in partially saturated rocks: Laboratory insights on free fluid index and comparison with borehole logs", SPWLA, 1991, 1pgs, Society of Petrophysicists & Well Log Analysts (Abstract).

Kuila et al., "Stress anisotropy and velocity anisotropy in low porosity shale", Tectonophysics, 2011, pp. 34-44, vol. 53, Elsevier.

Meissner et al., "State of the Art Special Core Analysis Program Design and Results for Effective Reservoir Management", International Petroleum Technology Conference, Doha, Qatar, 2009, 1pgs, (Abstract).

O'Meara Jr. et al., "Centrifuge Measurements of Capillary Pressure: Part 1—Outflow Boundary Condition", SPE, 1992, 1pgs, Society of Petroleum Engineers (Abstract).

Onitsuka et al., "A study on the relationship between mechanical properties and microstructure of Ariake Clay", ISOPE, 1999, 1pgs, The International Society of Offshore and Polar Engineers (Abstract).

Sarout et al., "Shale dynamic properties and anisotropy under triaxial loading: Experimental and theoretical investigations", Physics and Chemistry of the Earth, 2007, pp. 896-906, vol. 32, Elsevier.

Unalmiser et al., "Engineering Core Analysis", Distinguished Authors Series, 1998, pp. 106-112, SPE 36780.

Yao et al., Petrophysical characterization of coals by low-field nuclear magnetic resonance (NMR), Fuel, 2010, pp. 1371-1380, vol. 89, Elsevier.

Sze, et al.,"Physical Experimentation Research of Rock in Medium-Deep Natural Gas Reservoir", Chinese Maters Thesis Full-Text Database Basic Sciences; pp. A011-A041, vol. 3.

* cited by examiner

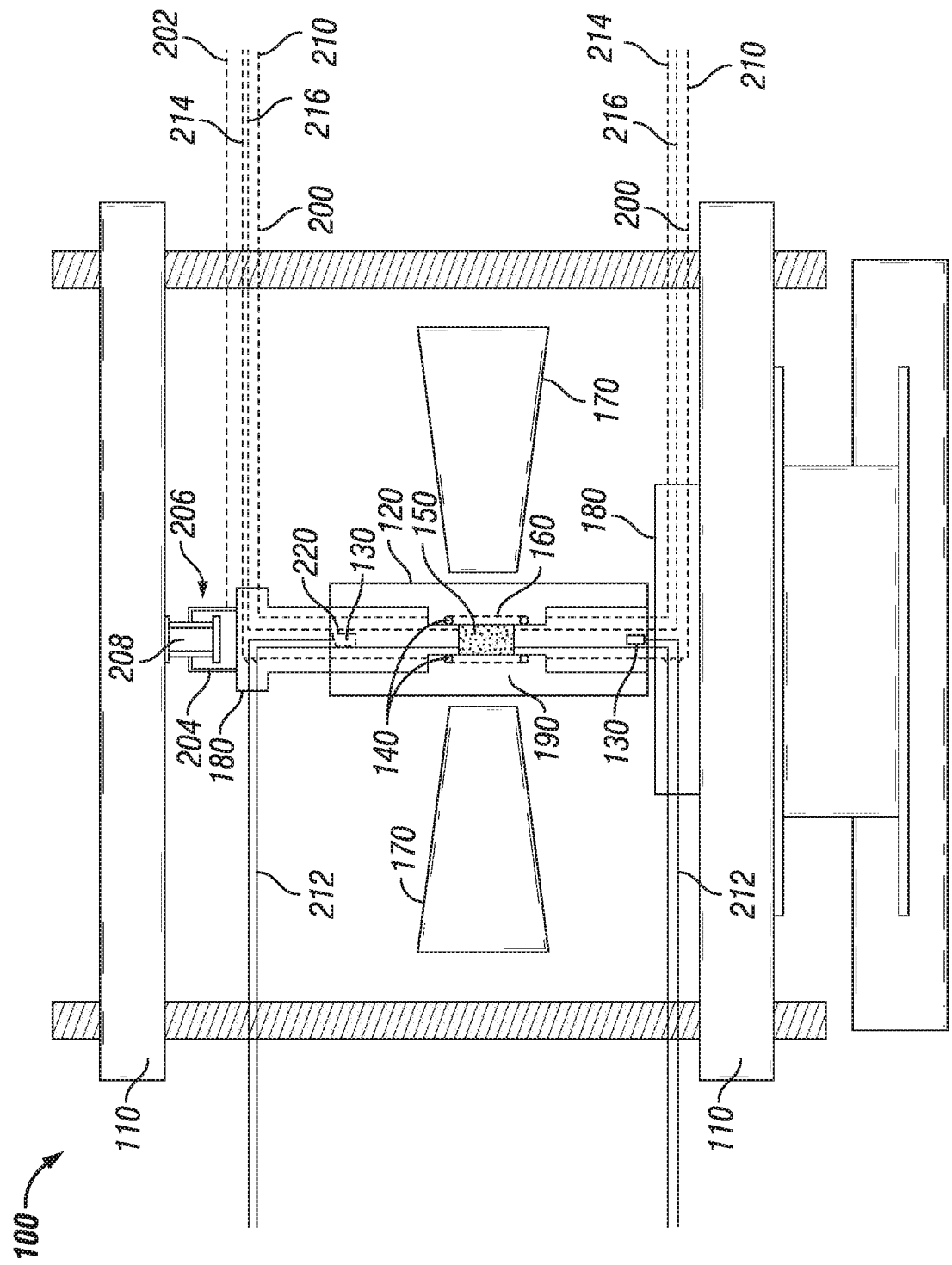

SYSTEMS AND METHODS FOR TRI-AXIAL NMR TESTING

CROSS REFERENCE TO RELATED APPLICATIONS

This application is a continuation in part of co-pending U.S. application Ser. No. 14/018,557 titled "Tri-Axial NMR Test Instrument," filed Sep. 5, 2013, the full disclosure of which is incorporated in this disclosure by reference in its entirety.

BACKGROUND OF THE DISCLOSURE

Field of the Disclosure

Generally, this disclosure relates to tri-axial nuclear magnetic resonance (NMR) testing with a tri-axial NMR test apparatus. The tri-axial NMR test apparatus is capable of assessing properties of various sample materials under reservoir temperature and pressure conditions.

Background of the Related Art

In the hydrocarbon industry it is important to evaluate downhole solid and fluid interactions at formation temperature and pressure conditions. As reservoir fluids are produced, temperature, pressure, fluid phase, fluid composition, and rock behavior is constantly changing due to changes in temperature, pressure, and other parameters. These changes can be modeled so that their effect on reservoir production can be understood.

Cementing of the wellbore is a critical processes during the life of a well. Cementing not only affects the production operation, but also leads to environmental issues related to gas migration and the contamination of water aquifers, and affects wellbore stability. The cement pumped into a wellbore undergoes a pumping, setting and curing cycle where uniform dispersion of material and fluids within the cement are critical aspects for a successful cementing job. The subterranean formation could have had millions of years for the temperature, pressures and fluid flow to stabilize. Cements used in a wellbore have to withstand the same reservoir conditions as the formation itself. The cement used for the wellbore should be evaluated at the same reservoir conditions that the cement will encounter after being pumped in a wellbore.

Other fluids used during various hydrocarbon development operations such as drilling, completion, intervention, and perforation fluids should be tested at the reservoir temperature and pressure conditions. As an example, fluids used during drilling operations perform a multitude of tasks such as lubrication of the bit, maintaining the temperature of the bit and drill string, providing a load on the bit so that the bit is pushed into the rock, providing pressure in the wellbore to mitigate any flow back or blowout of reservoir fluids, and pushing bridging material to penetrate and block the pores within the rock in the well bore being drilled. Understanding how such fluids act under reservoir conditions is important.

SUMMARY OF THE DISCLOSURE

Embodiments of this disclosure can provide test results based on data collected on reservoir retrieved core, cuttings, plugs, cement, and fluid samples. Systems and methods of this disclosure include collecting data on samples that are subjected to downhole pressures and temperatures. Current NMR test sample systems and methods lack the ability to generate such data under reservoir conditions. The collected data can be correlated to a broader set of data that is continuously acquired during logging, well testing, and seismic data gathering.

In an embodiment of this disclosure, a tri-axial nuclear magnetic resonance apparatus for testing properties of a test sample includes a tri-axial load frame encasing a tri-axial load cell and a piston assembly. The tri-axial load cell has a tri-axial sample holder and defines a radial space surrounding the tri-axial sample holder. The tri-axial load frame encases at least one end cap that is operable to contact the tri-axial load cell and a nuclear magnetic resonance instrument. An axial pressure line is in fluid communication with the piston assembly. A confining pressure line is in fluid communication with the radial space. A pore pressure line is in fluid communication with the test sample. The axial pressure line, the confining pressure line, and the pore pressure line are independent and separate fluid flow paths.

In alternate embodiments, the confining pressure line, and the pore pressure line can extend through the at least one end cap. The at least one end cap can include a conductor operable for electric current flow. The at least one end cap can further define one or more cavities for housing at least one acoustic sensor. The apparatus can be operable to maintain an axial pressure that is greater than a confining pressure and greater than a pore pressure. The test sample can be a fluid, a cement, a drill cutting, or a coal bed methane reservoir core.

In an alternate embodiment of this disclosure, a method of using the tri-axial nuclear magnetic resonance apparatus includes obtaining the test sample and loading the test sample into the tri-axial sample test holder. The tri-axial sample holder is loaded in the tri-axial load cell to create a loaded tri-axial load cell. An axial pressure is applied by providing axial pressure fluid through the axial pressure line. A confining pressure is applied by providing confining pressure fluid through the confining pressure line, the confining pressure being less than and independent of the axial pressure. Temperature control fluid can be circulated around the tri-axial sample holder by providing the temperature control fluid through the temperature control flow line. Data from the nuclear magnetic resonance instrument is measured.

In alternate embodiments the method can further include applying a pore pressure by providing a pore pressure fluid through the pore pressure line, where the pore pressure is less than and independent of both the axial pressure and the confining pressure. The axial pressure can be in an axial pressure range from 1 pounds per square inch (psi) to 500,000 psi, the confining pressure can be in a confining pressure range from 1 psi to 31,000 psi and the pore pressure can be in a pore pressure range of between about 1 psi and 30,000 psi.

In other alternate embodiments, the method can further include measuring data from an at least one acoustic sensor and at least one electrical sensor. The test sample can be a wellbore cement and the method can further include performing tests on the wellbore cement. The test sample can be a drill cutting and the method can further include performing tests on the drill cutting. The test sample can be a core from a coal bed methane reservoir and the method can further include performing tests on the core from the coal bed methane reservoir.

BRIEF DESCRIPTION OF THE DRAWING

So that the manner in which the recited features, aspects and advantages of the embodiments of the disclosure, as well as others that will become apparent, are attained and can be understood in detail, a more particular description of the disclosure briefly summarized in this disclosure may be had by reference to the embodiments that are illustrated in the drawing that forms a part of this specification. It is to be noted, however, that the appended drawing illustrates only certain embodiments of the disclosure and are not to be considered limiting of the disclosure's scope, for the disclosure may admit to other equally effective embodiments.

The FIGURE is a tri-axial NMR apparatus in accordance with an embodiment of the disclosure.

DETAILED DESCRIPTION

Although the following detailed description contains many specific details for purposes of illustration, it is understood that one of ordinary skill in the art will appreciate that many examples, variations and alterations to the following details are within the scope of the disclosure. Accordingly, embodiments described in this disclosure and provided in the appended FIGURE are set forth without any loss of generality, and without imposing limitations on the claimed embodiments.

The disclosure generally relates to core analysis, fluid analysis, petro-physical analysis and phase behavior evaluation of hydrocarbon reservoirs under tri-axial stress conditions with pore pressure. The tri-axial NMR apparatus described herein perform multiple tests on a sample at the same time and also integrate the data collected related to various sample properties. The apparatus allows for reservoir modeling. For example, when collecting acoustic data, such as sonic data, during NMR measurements, the apparatus will provide information regarding the mechanical stress changes on the sample not only as a function of pressure change, but also as the formation fluid changes. This information is directly used during seismic monitoring of reservoir production and for tuning simulation models for production profiles.

In one aspect, the disclosure provides the tri-axial nuclear magnetic resonance apparatus for testing of petro-physical properties and gathering of geo-mechanical information. The tri-axial nuclear magnetic resonance apparatus includes a tri-axial load frame encasing a tri-axial load cell having a tri-axial sample holder and a radial space surrounding the tri-axial sample holder. At least one end cap is operable to contact the tri-axial load cell. The apparatus also includes at least one electrical sensor, at least one acoustic sensor, and the nuclear magnetic resonance instrument.

The tri-axial load cell includes the tri-axial sample holder. The tri-axial sample holder can be made of any material acceptable for a tri-axial sample holder. In general, the tri-axial sample holder will either have no NMR signature, or a known NMR signature. In certain embodiments, the tri-axial sample holder is made of TORLON® (available from Solvay Plastics). TORLON® has a sufficient pressure and temperature rating and is "invisible" to the NMR. The tri-axial sample holder can be designed such that it has no orifices for fluid or electrical connection on the outer surface. In some embodiments, the design of the tri-axial sample holder is such that the tri-axial sample holder is free of any connection on the outer face of the tri-axial sample holder. This design provides greater hoop strength for greater confining pressures. This design has additional benefits of reducing the wall thickness of test vessel, allowing a larger diameter sample to be used.

In some embodiments, the tri-axial sample holder is in the shape of a cylinder. In further embodiments, the diameter of the cylinder can be from about 2.5 millimeters (mm) to about 102 mm. The length of the cylinder can be from about 2.5 mm to about 508 mm. In general, the tri-axial sample holder is capable of withstanding the level of stresses associated with generating fractures in the reservoir and is capable of applying axial stress equal to the stresses found in reservoirs.

The tri-axial load cell can provide axial pressure independent of confining and pore pressure. The tri-axial load cell is connected to a pump and pressure gauge for applying and monitoring the axial stress on the sample loaded into the tri-axial sample holder. The tri-axial load cell can be used to initiate fractures in a sample to study fracture mechanics with fluid transport. In some embodiments, the tri-axial load cell is made of coated titanium.

The tri-axial load cell further includes pore pressure lines, acoustic sensor feeds, and electrical sensor feeds. The pore pressure lines, acoustic sensor feeds, and electrical sensor feeds can be located on or in the end caps. The fluid for both confining pressure and pore pressure is provided through the at least one end cap on the tri-axial load cell. In some embodiments, there are two end caps. The end caps can be floating end caps that can accommodate various lengths of samples within the same tri-axial sample holder.

The end caps can accommodate the pressure lines to allow for fluid flow. The pressure lines allow for fluid flow into the radial space surrounding the tri-axial sample holder, into the tri-axial sample holder, and into the piston assembly. Fluid flow can be provided through the pressure lines using injection, application, or any other supply mechanism known to those of skill in the art. In some embodiments, the end caps have three pressure lines. In some embodiments, the end caps are made of aluminum or TORLON®.

In further embodiments, the end caps are embedded with a conductor that allows for electric current flow. Any acceptable conductor can be used. In certain embodiments, the conductor is selected from gold, platinum, or aluminum. The end caps further include one or more cavities for housing the at least one acoustic sensor.

The tri-axial load frame encases the components of the apparatus. In general, the tri-axial load frame should either have no NMR signature, or a known NMR signature. In some embodiments, the tri-axial load frame is made from titanium with an additional coating for increasing inertness to NMR and to handle corrosive chemicals, acids, and industrial solvents that may be used during testing. Such chemicals include toluene, methanol, chloroform, carbon dioxide in liquid, gas, or liquid and gas states, methane, water, xylene, hydrochloric acid, and acetic acid. In further embodiments, the tri-axial load frame is expandable to accommodate longer samples. In some embodiments, the tri-axial load frame also encases deformation measurement devices such as a linear variable differential transformer, a strain gauge, and an infrared or acoustic displacement system to measure static mechanical properties of the sample.

In further embodiments, the tri-axial load cell is equipped with a piston separator to perform various pressure-volume-temperature analyses, such as viscosity, compressibility, constant composition expansion, wax, asphaltene, and hydrate formation. In one embodiment, if the sample is a fluid and a specific NMR probe is used, then it is possible to detect asphaltene as function of carbon-13. It is also possible to identify hydrate structure, which is a desirable aspect of hydrate production and mitigating flow assurance, as well bore stability issues related to wax, asphaltene, hydrate, and salt crystallization.

In some embodiments, the at least one electrical sensor is a resistivity probe which provides electrical property measurements at the same time as other properties are measured. This assists in integration of various lab and field data for both rock and fluids of the reservoir. In some embodiments, the fluid and associated pore line on the ends of the tri-axial sample holder can be used to measure electrical response. In instances of a non-conductive fluid, non-magnetic conductors may be installed on the sample during sample preparation for the purpose of electrical property measurements. In some embodiments, an impedance analyzer can be used to assess the voltage, current, phase, and resistivity of the sample.

In some embodiments, the acoustic sensor is an acoustic transducer with variable frequency and mode, such as shear and longitudinal. Various mode transducers, along with variable frequency, allow the analysis to target specific pore size, grain size, or fluid components. The acoustic transducer measures various dynamic properties of the sample under tri-axial conditions with accurate fluid saturation and an easy path for log data integration. In some embodiments, the at least one acoustic sensor is operable to function as a transmitter and a receiver. Among the acoustic properties that may be measured include the P-wave, which is longitudinal, and S-wave, which is shear at 180, 90, and 45 degree angles both in transmission and reflection mode, and travel time, along with the complete frequency spectra. Dual mode transducers may be selected based on the sample size and test procedure, with frequency ranges from a number of kilohertz (KHz) used in logging tools for bulk properties of rock and fluid to greater frequency ranges in order to investigate detailed diffusion patterns and pore geometries with the test samples. Many such transducers are readily available. Additionally, a person of skill in the art may also specially design a transducer based on specific sample parameters under investigation.

By having the capability of performing acoustic measurements with various modes with the tri-axial NMR apparatus, there is increased understanding of formation damage due to sand migration, and formation damage due to wax and asphaltene drop out as temperature and pressure changes. Such measurements will also assist in assessment of provided fluid interaction with the rock matrix, especially in chemical enhanced oil recovery (EOR), as the tri-axial capability helps mimic the stress regime in a given reservoir more so than the conventional hydrostatic test vessels currently available. The additional acoustic and resistivity measurements also provide a suitable method for calibrating field log data before and after EOR on a specific field.

The NMR instrument can be any NMR appropriate for these particular applications. In general, a large bore NMR with suitable signal to noise ratio, and signals received with minimum time delay, is acceptable. In general, the NMR should have the gradient and appropriate bore diameter for the tri-axial load cell. A NMR with a proper combination of gradient and reduced time delay will provide not only a saturation profile between the hydrocarbon and non-hydrocarbon fluids, but will also identify bound and free water, assist in differentiating between oil and kerogen, and may assist in differentiating between kerogen hydrocarbon gases and asphaltene.

The NMR can have capability to perform both whole and thin slice scanning. The capability of performing focused NMR scanning on a smaller area will provide more detail features of the sample. The technique can be used to measure the permeability of an unconventional tight reservoir and will be able to differentiate between matrix permeability, fracture permeability, and diffusivity of various fluids. A fluid will be provided to one face of the sample and time dependent slice NMR scanning will be performed to see the movement and shape of the front providing valuable transport behavior of the reservoir sample. In some embodiments, the tri-axial NMR apparatus will be equipped with a controlled positioning device, or cell mobilizer to provide accurate and repeatable slice location. This can be achieved for a shorter sample by moving a window between the NMR borehole and test vessels and for longer sample, the whole NMR can be mobilized to provide slice scans. The NMR has the capability to perform NMR scans from a 0.1 mm slice to 152.4 mm slice, for 360 degrees. Additionally, the NMR can have a variable magnetic field and frequency ranging from a number of KHz to a number of megahertz (MHz). This range will assist in focusing on various rock and fluid constituent in detail.

The NMR can also have a variable probe for hydrogen, carbon-13, sodium, and other components that are likely to occur in a reservoir. Such a probe will focus testing on various components of the rock fabric and fluids. For example, a sodium probe scan along with a hydrogen probe scan will amplify the difference between free water and bound water, as well as provide information about the salinity of the formation. Similarly, a carbon-13 probe can help in identifying maturity and type of kerogen in a sample.

In further embodiments, the tri-axial nuclear magnetic resonance apparatus has pore-pressure capability which allows for raising fluid pressure to reservoir conditions. Additionally, this setup allows for the measurement of permeability in both a steady state and an un-steady state with dead or live fluids. Steady state is a relative permeability test where two or more fluids are provided simultaneously at one end of a cylindrical plug sample of reservoir rock and the change in sample fluid saturation is monitored as a function of fluid produced on the other end to mimic reservoir injection. Un-steady state is a test where one fluid is provided in the rock plug sample in the presence of a second fluid inside the sample and production of both fluids is monitored on the other end of the sample. This mimics how the reservoirs were formed initially and is also the mechanism of primary oil production. Dead fluid is fluid with no, or a very small amount of, gas. Live fluid is fluid with gas at the same chemical composition as found in a given hydrocarbon reservoir.

In further embodiments, the tri-axial nuclear magnetic resonance apparatus can also include one or more semi-permeable membranes for analyzing capillary pressure and wettability measurements. In one configuration of the instrument setup, one or more porous semi-permeable membranes can be incorporated to perform capillary pressure and wettability analysis of a reservoir sample under tri-axial test conditions with NMR saturation and other measurements. There are many advantages of performing such an analysis, beyond the use for data integration. One major advantage of such an analysis is to tune various empirical equations used for the simulation of reservoirs with real data.

In further embodiments, the tri-axial nuclear magnetic resonance apparatus can also include feeds to a second NMR for injection and production fluid evaluation under stress conditions. This has added value for performing detailed research to evaluate various nano technology fluids and other phase behavior attributes of reservoir or injected fluids.

The tri-axial nuclear magnetic resonance apparatus includes a pressurized fluid circulation system to maintain a temperature during testing with a temperature control fluid.

The tri-axial nuclear magnetic resonance apparatus further includes pumps for providing various stresses for sample and fluid flow.

In some embodiments, the tri-axial nuclear magnetic resonance apparatus includes a sample strain measurement system or displacement measurement device. Such a sample strain measurement system or displacement measurement device could be electrical, infrared, acoustical, or any other kind based on sample and test condition requirements. The advantage of performing strain measurements on a reservoir rock sample is that it relates to mechanical strength and formation damage issues. The advantage of performing strain measurements on a fluid sample is that it relates to production profiles and flow assurance issues.

The tri-axial nuclear magnetic resonance apparatus can also include a suitable densitometer and viscosity meter at the injection and production ends for transport behavior evaluation. These types of meters provide valuable information about fluid property change during a core sample test. For instance, these tests may show that at different pressure and flow rates the possibility of emulsification of injected fluid and the rock matrix.

In further embodiments, the tri-axial nuclear magnetic resonance apparatus includes an acoustic separator on the production end for production measurements. Acoustic separators are known by persons of skill in the art. Such persons could readily select an appropriate acoustic separator for use in this disclosure.

In further embodiments, the tri-axial nuclear magnetic resonance apparatus includes a cylinder and fluid rocking system for live fluid injection. Cylinder and fluid rocking systems are known by persons of skill in the art. Such persons could readily select an appropriate cylinder and fluid rocking systems for use in this disclosure.

In further embodiments, the tri-axial nuclear magnetic resonance apparatus includes sensitive pressure sensors for various sample and fluid pressure monitoring. Sensitive pressure sensors are known by persons of skill in the art. Such persons could readily select an appropriate sensitive pressure sensor for use in this disclosure.

The FIGURE shows a tri-axial NMR apparatus 100 according to an embodiment of the disclosure. This embodiment of the apparatus has tri-axial load frame 110. The apparatus further includes tri-axial load cell 120, NMR apparatus 170, end caps 180, acoustic sensors 130, electrical sensors 140, tri-axial sample holder 150, pressure lines 200, conductors 212, and cavity 220. Optionally, isolation jacket 160 may be added to surround the tri-axial sample holder. Additionally, shown is radial space 190 surrounding the tri-axial sample holder.

The acoustic sensors 130 and electrical sensors 140 are spaced away from the sample so that the NMR apparatus has an unobstructed view of the sample.

In an example of operation, a method of using the tri-axial nuclear magnetic resonance apparatus includes obtaining a test sample, loading the test sample in the tri-axial sample holder, and loading the tri-axial sample holder in the tri-axial load cell to create a loaded tri-axial load cell. If the sample is a solid sample such as a core, cuttings, plugs, or cement sample then the sample can be loaded into the tri-axial load cell as an intact sample that has not been crushed. After a sample has been crushed, the sample can no longer be stressed back to reservoir conditions. In addition, in order to applying a confining stress on a solid sample, the sample must have a defined circumference and for applying an axial load on a solid sample, the sample should have a generally planar end surface.

The loaded tri-axial load cell is then placed in contact with at least one end cap of the tri-axial nuclear magnetic resonance apparatus. A tri-axial pressure is then applied to the tri-axial load cell. The tri-axial pressure can include the axial pressure and the confining pressure. In certain embodiments, the tri-axial pressure can further include the pore pressure. In order to apply the axial pressure, an axial pressure fluid is applied by way of axial pressure line 202 and into piston chamber 204. Piston chamber 204 is part of piston assembly 206. Piston assembly 206 includes piston member 208 that engages a structural member of tri-axial load frame 110. Piston chamber 204 engages end cap 180. As axial pressure fluid is delivered into piston chamber 204 end cap 180 is pushed axially away from piston member 208 so that end cap 180 applies axial pressure on the sample.

In order to apply the confining pressure a confining pressure fluid is applied through the at least one end cap by way of confining pressure line 214 and into radial space 190 that surrounds the sides of the sample to apply a confining pressure on the sample. In order to apply the pore pressure a pore pressure fluid is applied through the at least one end cap by way of pore pressure line 216 and into contact with the sample to apply a pore pressure on the sample. The axial pressure line, the confining pressure line, and the pore pressure line are independent and separate fluid flow paths.

Alternately, the test sample can be a fluid or a fluid that contains some solids or gas, such as a cement slurry, drilling fluids, reservoir fluids, or EOR chemicals. In such an embodiment the fluid test sample can be injected through the pore pressure line 216 and into tri-axial sample holder. As the fluid test sample is introduced into the tri-axial sample holder, one or more of the endcaps 180 are pushed in a direction away from the other of the endcaps until the fluid sample to be tested is located within the tri-axial sample holder. After the fluid sample to be tested is located within the tri-axial sample holder, the pressure of the fluid sample is maintained at a pressure less than the axial pressure and the confining pressure.

The flow path for the axial pressure fluid is separate and independent from the flow path for the confining pressure fluid and separate and independent from the flow path for the pore pressure fluid. The axial pressure is applied independent of the confining pressure and the pore pressure. Similarly, the confining pressure fluid is separate and independent from the flow path for the pore pressure fluid.

During operation of the tri-axial NMR apparatus 100, the axial pressure is applied and maintained at a magnitude that is greater than the confining pressure. Where there is a pore pressure, the axial pressure is applied and maintained at a magnitude that is greater than the pore pressure. Having the ability to independently adjust the axial pressure, the confining pressure and the pore pressure allows for the simulation of the true tri-axial stress conditions that are observed in hydrocarbon reservoirs. The independent axial stress being greater than the confining stress is responsible for changes in pore throat structure that controls fluid mobility in actual subterranean reservoirs. In the reservoir, rocks and fluids are under tri-axial conditions where axial pressure is greater than confining and pore pressure, and pore pressure is less than confining pressure. If pore pressure was greater than confining pressure the reservoir would fracture and fail. Only by duplicating these conditions can the sample be tested at replicate downhole pressures.

A temperature control fluid can then be circulated around the loaded tri-axial sample holder by providing the temperature control fluid through the at least one end cap to the radial space surrounding the tri-axial sample holder. The temperature control fluid can be delivered by way of temperature control flow line 210 to maintain the temperature of the tri-axial sample holder during analysis. A test fluid can then provided to the loaded tri-axial sample holder through the at least one end cap by way of the pressure lines. A time dependent slice nuclear magnetic resonance scan of the sample is performed using the nuclear magnetic resonance instrument. Electrical analysis of the sample using the at least one electrical sensor and acoustical analysis of the sample using the at least one acoustic sensor are also performed.

The samples can be obtained from any reservoir. Reservoirs from which the sample can be obtained include unconventional reservoirs, such as shale gas, tight gas sand, heavy oil, tar sand, hydrates and depleted enhanced oil recovery reservoirs. The samples used for analysis can be a native sample or a clean sample. The term native sample means a reservoir rock plug sample that has been drilled and retrieved from reservoir and installed in the tri-axial sample holder without any alternation. The term clean sample means a sample that, after having been retrieved from a reservoir, has gone through various processes to remove all fluids and associated solids, such as salt, wax, and asphaltene.

Tri-axial pressures can include any combination of the following pressures: axial pressure, confining pressure, and pore pressure. In some embodiments, axial pressure ranges from about 1 psi to about 500,000 psi, pore pressure ranges from about 1 psi and 30,000 psi, and confining pressure ranges from about 1 psi and 31,000 psi. The pore pressure for the sample should be at least about 100 psi less than the confining and axial pressures. In general, the pressures are selected such that they mimic conditions of the reservoir being studied.

During analysis, the temperature of the tri-axial sample holder can be controlled to mimic conditions of the reservoir being studied. In some embodiments, the temperature can be controlled using a temperature control fluid. Acceptable temperature control fluids include any known temperature control fluids that have a minimum known, or no, effect, on the NMR signal. In some embodiments, the tri-axial sample holder is maintained at a temperature of between about −20 degrees Celsius (° C.) and 350° C. In general, the temperature is selected based on the temperature conditions in the reservoir or other material being studied.

The test fluid provided to the loaded tri-axial sample holder through the at least one end cap includes a variety of fluids. "Provided" indicates that the test fluid is injected, applied, or otherwise supplied to the tri-axial sample holder. For instance, solvents such as toluene, methanol, chloroform, xylene, water, and carbon dioxide can be provided for leaching of hydrocarbons and salts. Acids of varying concentrations can be provided for cleaning and simulations. Hydrocarbon liquids, gases, and brine solutions can be provided for flow capacity measurements. Wettability EOR chemicals can be provided for simulations. Fracturing fluids with propants can be provided for simulations. In some embodiments, the test fluid is a dead fluid. In other embodiments, the test fluid is a live fluid.

In some embodiments, the time dependent slice nuclear magnetic resonance scan of the sample measures nuclear magnetic frequencies from about 0.1 KHz to 20 MHz. The frequency will be selected based on the type of sample being assessed and the parameters being studied. For example, for a homogenous single pore type sample with fluid with a viscosity in a range of 0.5 to 2.0 centipoise (cP) viscosity, a 2 MHz nuclear magnetic frequency may be acceptable. However, for a more viscous fluid with a heterogeneous rock pore system with multiple pore type, a combination of 2 MHz and 12 MHz nuclear magnetic frequencies may be needed. In further embodiments, the nuclear magnetic resonance instrument is equipped with variable probes for performing analysis on the samples.

The acoustic analysis of the sample measures frequencies from about 1 hertz (Hz) to 100,000 MHz. The size of the sample may dictate the frequency. For instance, for an average sized sample, the range may be between 500 KHz to 1 MHz. For a smaller sized sample, a frequency greater than 1 MHz may be necessary. Larger sample sizes may require less than 500 MHz.

Various embodiments of this disclosure will reduce the turnaround time for reservoir evaluation. By performing multiple analyses together, there will be significant operational benefits of time savings. Additionally, data accuracy will be improved and integration to field and log data will improve. Embodiments of the present disclosure will provide a comprehensive study platform for EOR and shale gas analysis.

The tri-axial NMR instrument has the capability of performing a number of different tests. Among the tests that could be performed are: NMR test under tri-axial conditions with no pore pressure; NMR test under tri-axial conditions with pore pressure; NMR test under hydrostatic condition with or without pore pressure; NMR test with a combination of tri-axial, hydrostatic, unconfined, pore pressure, acoustic, electrical, temperature, slice NMR, whole NMR, deformation measurement, stress changes (axial, confining, pore), fluids (acoustic, density, electrical measurements), fluid (pressure, volume, temperature, flow rate and components measurements (in flow and out flow)); NMR tests with mechanical tests and combination of sensors; NMR tests with steady state permeability test, tri-axial conditions and sensors for various petro-physical and geo-mechanic data; NMR tests with un-steady state permeability test, tri-axial conditions and sensors for various petro-physical and geo-mechanic data; NMR tests with plate (membrane) capillary pressure test, tri-axial conditions and sensors for various petro-physical and geo-mechanic data; NMR tests for EOR, steam-assisted gravity drainage, water alternating gas, carbon dioxide, chemicals, surfactant, steam, and acid treatments; NMR tests on fluids such as heavy oil, hydrates, asphaltene amounts, and crystallization under hydrostatic conditions; NMR tests with pressure, volume and temperature (constant composition expansion, Differential liberation), and flow assurance studies under hydrostatic condition.

An example test procedure is described as follows:
1. Prepare the tri-axial nuclear magnetic resonance apparatus and perform system calibrations.
2. Prepare test specimens.
3. Prepare the NMR instrument setup based on the type of test and sample, such as whether the sample is from a core material or a fluid sample.
4. Prepare the correct NMR probe and perform base calibrations.
5. Install the sample into the tri-axial sample holder. Install the tri-axial sample holder in the tri-axial load cell. Install the tri-axial load cell in the NMR apparatus using the end caps and connect all the feeds for fluids and data sensors.
6. Apply initial axial pressure of about 50 psi. However, this step could be modified based on sample elastic properties. For example, core samples can be CTscanned to indicate whether a sample is soft or strings. For stronger samples, the initial pressure may start at 1000 psi or greater.

7. Hold the axial displacement and increase confining and pore pressure on the sample until sample has reached test pressures. This step could be modified bases on the sample used and the desired test procedures.
8. Circulate temperature control fluid around the tri-axial sample holder and monitor sample temperature and pressure along with other data such as acoustic information and strain resistivity.
9. Once the sample has reached required test conditions and all the test parameters are in pseudo equilibrium mode such as within acceptable fluctuations based on specific test parameters, commence the test.
10. During the test, monitor all the sensors, pressures, and test parameters to measure and gather acoustical, electrical, NMR and other data.
11. Perform tests on test specimen and gather data from the sensors.
12. Analyze data collected.
13. Unload the samples carefully, bring temperature down to ambient or near ambient temperatures and then reduce the various pressures in a manner so as to maintain sample integrity.

In an example of operation, the sample can be drill cuttings. During field operations, drill cuttings are constantly generated and are sent to mud pit where an on-field engineer can visually look at them for hydrocarbon evidence. Drill cuttings hold a wealth of information within them that have exponentially increased value when the cuttings are analyzed soon after they reach the surface. As an example, one of the most important parameters for evaluating the size of a hydrocarbon discovery is the amount of hydrocarbon compared to the non hydrocarbon fluids, such as water.

As time passes the cuttings get dried or fluids are lost or rearranged with the cutting porous structure. The value of data gathered from the cuttings decreases exponentially over time and can provide incorrect results if too much time passes before the cuttings are evaluated. When these cuttings or when a core reaches a lab in hours, days, or weeks and are analyzed some times after months, the quality of data is lost. The tri-axial NMR apparatus of this disclosure can be used on site and quickly apply the reservoir pressures on the field plugs or cuttings samples to bring the samples back to reservoir conditions and can perform measurements to provide data related to fluid types, fluids saturation, location of fluids, their electrical response, sonic response and other sets of valuable data in a timely manner.

In an alternate example of operation, the sample can be a core or cutting of a coal bed methane reservoir. A current practice for testing samples from a coal bed methane reservoir involves two separate test steps with two separate instruments. The first test involves cutting a core of material and keeping the core under water in test vessels under ambient pressure for months to estimate gas evaluation. The second test includes crushing a piece of the core and collecting gas emitted from that process. In this process, an amount of methane escapes. In addition, the crushed piece might not accurately represent the coal sample as a whole which can lead to an error in the estimation of the amount of methane resource of the reservoir.

The tri-axial NMR apparatus can instead perform both tests with a single instrument on the same sample and at actual reservoir temperature and pressure conditions. In addition, the tri-axial NMR apparatus can be used to:

a. better understand the flow of methane flow through fractures of the reservoir,
b. understand the desorption process at a given temperature and stress condition,
c. evaluate a rate of desorption and production as function of change in stresses,
d. better understand the process water drive to inhibit pores once the methane has been liberated,
e. study the effect of water injection on the desorption and production of methane,
f. evaluate the matrix compared to fracture permeability as a function of stress, temperature, and desorption,
g. use a pore pressure injection method to create a fracture and evaluate propant placement, fracture closing, fracture fluid dispersion, propant flow back, propant failure or crushing, propant capacity to maintain fracture as function of stress and flow, and propant embedment with the formation,
h. use an independent axial stress piston to create a mechanical fracture and study fluid flow,
i. use an independent axial stress piston to crush the whole specimen and gather residual gas information, or
j. to use the intact core or crushed core to study the adsorption process of methane for studying the total maximum capacity of the reservoir for understanding maturity or migration of methane.

In another alternate example of operation, the sample can be a cement or drilling fluid used for the hydrocarbon development and tested at downhole temperature and pressure conditions. The tri-axial NMR apparatus can be used to test the sample at downhole temperature and pressure conditions to:

a. determine cement thickening time test under downhole tri-axial conditions,
b. determine cement setting and curing time and record of dynamic changes before, during and after curing and setting,
c. measure free water before and after the cement is set to evaluate cement hydration and seal capacity,
d. inject fluid into the sample to evaluate permeability of cement matrix,
e. measure seal strength and effectiveness between cement and reservoir rock and casing material,
f. measure solid, liquid, or gas additive dispersion during the setting and curing of cement,
g. perform a hydrostatic compressive strength test on set cement and determine leakage and seal capacity during various stages before failure and after failure,
h. perform a tri-axial compressive strength test on set cement and determine leakage and seal capacity during various stage before failure and after failure,
i. determine Poison ratio and Young modulus of cement both static and dynamic,
j. determine the effect of drilling fluid on bonding capacity of cement to reservoir rock and casing,
k. determine the effect of acidizing and fracturing fluid on cement,
l. study gas migration,
m. measure electrical properties and sonic velocity for calibrating bond logs,
n. determine the effect on drilling fluid properties as function of temperature and pressure change,
o. determine the effect on rheology of drilling fluids as the function of rate of circulation and temperature or pressure between the pump to the drill bit,
p. evaluate the crystallization of salt material and solid drop out, q. rate the bridging capacity for drilling fluid,
r. determine the thickness of a mud cake with drilling fluid circulation,
s. rate filtrate generation and penetration in the reservoir, and
t. to determine the effect on the drilling fluid capacity to carry drill cuttings.

In some embodiments, the present disclosure provides density, NMR, resistivity, and acoustic measurements of provided and produced fluids as a single phase fluid at reservoir conditions. For instance, in some cases, the fluid is made of a hydrocarbon liquid and gases at a certain pressure and temperature. A drop in either temperature or pressure can convert a single phase fluid into the gas and liquid phases. Thus, testing of the samples at reservoir conditions allows for more accurate assessment of the mixed gas and liquid samples, as they exist at reservoir conditions. In further embodiments, the present disclosure also provides density, NMR, resistivity, acoustic and volume measurements of each separated phase (oil, brine, gas, EOR agent), at selected temperature and pressure. In further embodiments, the present disclosure provides measurement of sample deformation as function of stress.

Another use of the tri-axial NMR apparatus will be to integrate the data of the NMR test and measurement to the sonic, resistivity (induction log), gamma and porosity (neutron logs), and geochemical logs. The data may then be extrapolated to wells where samples have not yet been analyzed.

Another use of the tri-axial NMR apparatus relating to fluid analysis is the accurate determination of saturation (bubble point) pressure during a constant composition expansion (CCE) test. The added advantage could be identification of phases, if more than one exists, with the combination of NMR, acoustic measurements, and electrical measurement at the same time. The advantage of doing a CCE test using the tri-axial NMR apparatus as compared to existing methods is that it can provide a time dependent separation and segregation of various fluids based on their densities. Such data can assist in reservoir production close to saturation pressure and for condensate reservoirs analysis.

Although embodiments of this disclosure has been described in detail, it should be understood that various changes, substitutions, and alterations can be made hereupon without departing from the principle and scope of the disclosure. Accordingly, the scope of the disclosure should be determined by the following claims and their appropriate legal equivalents.

The singular forms "a," "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value to about another particular value. When such a range is expressed it is to be understood that another embodiment is from the one particular value to the other particular value, along with all combinations within said range. Additionally, the ranges should be understood to include all values that are understood by a person of skill in the art as being within the scope of the disclosure, including all values that are deemed equivalents, the same, or nearly the same as the particular values being described.

As used herein and in the appended claims, the words "comprise," "has," and "include" and all grammatical variations are each intended to have an open, non-limiting meaning that does not exclude additional elements or steps.

What is claimed is:

1. A method of testing properties of a test sample with a tri-axial nuclear magnetic resonance apparatus, the method including:
   providing the tri-axial nuclear magnetic resonance apparatus having:
     a tri-axial load frame encasing:
     a tri-axial load cell having a tri-axial sample holder and defining a radial space surrounding the tri-axial sample holder;
     a piston assembly;
     at least one end cap operable to contact the tri-axial load cell;
     a nuclear magnetic resonance instrument located external of the tri-axial load cell; and
     an axial pressure line in fluid communication with the piston assembly, a confining pressure line in fluid communication with the radial space, and a pore pressure line in fluid communication with the test sample, where the axial pressure line, the confining pressure line, and the pore pressure line are independent and separate fluid flow paths so that all pressure surfaces of the piston assembly are free of fluid communication with the tri-axial load cell;
   obtaining the test sample;
   loading the test sample into the tri-axial sample holder;
   loading the tri-axial sample holder in the tri-axial load cell to create a loaded tri-axial load cell;
   applying an axial pressure by providing an axial pressure fluid through the axial pressure line;
   applying a confining pressure by providing the confining pressure fluid through the confining pressure line, the confining pressure being less than and independent of the axial pressure;
   circulating temperature control fluid around the tri-axial sample holder by providing the temperature control fluid through a temperature control flow line to the radial space; and
   measuring data from the nuclear magnetic resonance instrument; where
   the at least one end cap includes two end caps, with one of the two end caps contacting a first end of the tri-axial load cell, and an other of the two end caps contacting a second end of the tri-axial load cell that is opposite the first end;
   applying an axial pressure includes providing an axial pressure fluid through the axial pressure line; and
   applying a confining pressure includes providing the confining pressure fluid through the confining pressure line that extends through both of the two end caps.

2. The method of claim 1, further including applying a pore pressure by providing a pore pressure fluid through the pore pressure line, where the pore pressure is less than and independent of both the axial pressure and the confining pressure.

3. The method of claim 1, where the tri-axial load cell is operable to provide an axial pressure of up to 500,000 psi; a confining pressure of up to 31,000 psi; and a pore pressure of up to 30,000 psi.

4. The method of claim 1, where the method further includes measuring data from an at least one acoustic sensor and at least one electrical sensor; where the at least one end cap contacts the tri-axial load cell and further defines one or more cavities for housing the at least one acoustic sensor, and where the electrical sensor is located within the tri-axial load cell and spaced away from the test sample.

5. The method of claim 1, where the test sample is a wellbore cement and the method further includes testing the wellbore cement at downhole temperature and pressure conditions.

6. The method of claim 1, where the test sample is a drill cutting and the method further includes testing the drill cutting at downhole temperature and pressure conditions.

7. The method of claim 1, where the test sample is a core from a coal bed methane reservoir and the method further includes testing the core from the coal bed methane reservoir at reservoir temperature and pressure conditions.

* * * * *